(12) United States Patent
Northen et al.

(10) Patent No.: US 9,512,065 B2
(45) Date of Patent: Dec. 6, 2016

(54) POLYMORPHS OF N-[(R)-1-[(S)-1-(4-AMINOMETHYL-BENZYLCARBAMOYL)-2-PHENYL-ETHYLCARBAMOYL]-2-(4-ETHOXY-PHENYL)-ETHYL]-BENZAMIDE HYDROCHLORIDE

(71) Applicant: Kalvista Pharmaceuticals Limited, Porton Down (GB)

(72) Inventors: Julian Scott Northen, Sunderland (GB); John Mykytiuk, Sunderland (GB)

(73) Assignee: Kalvista Pharmaceuticals Limited, Porton Down (GB)

( * ) Notice: Subject to any disclaimer, the term of this patent is extended or adjusted under 35 U.S.C. 154(b) by 0 days.

(21) Appl. No.: 14/413,086

(22) PCT Filed: Jul. 5, 2013

(86) PCT No.: PCT/GB2013/051781
§ 371 (c)(1),
(2) Date: Jan. 6, 2015

(87) PCT Pub. No.: WO2014/006414
PCT Pub. Date: Jan. 9, 2014

(65) Prior Publication Data
US 2015/0191421 A1    Jul. 9, 2015

Related U.S. Application Data

(60) Provisional application No. 61/668,543, filed on Jul. 6, 2012.

(30) Foreign Application Priority Data

Jul. 6, 2012 (GB) .................................. 1212081.2

(51) Int. Cl.
C07C 237/22 (2006.01)
C07C 231/24 (2006.01)

(52) U.S. Cl.
CPC ........... *C07C 237/22* (2013.01); *C07C 231/24* (2013.01); *C07B 2200/13* (2013.01)

(58) Field of Classification Search
None
See application file for complete search history.

(56) References Cited

U.S. PATENT DOCUMENTS

| 5,187,157 A | 2/1993 | Kettner et al. |
| 2014/0213611 A1* | 7/2014 | Evans .................... C07C 237/22 514/311 |
| 2015/0225450 A1* | 8/2015 | Evans .................... C07C 237/22 514/20.3 |

FOREIGN PATENT DOCUMENTS

| EP | 2281885 | 2/2011 |
| WO | WO 92/04371 | 3/1992 |
| WO | WO 94/29335 | 12/1994 |
| WO | WO 95/07921 | 3/1995 |
| WO | WO 03/076458 | 9/2003 |
| WO | WO 2004/062657 | 7/2004 |
| WO | WO 2008/016883 | 2/2008 |

(Continued)

OTHER PUBLICATIONS

Chemical & Engineering News, Feb. 24, 2003, pp. 32-35.*

(Continued)

*Primary Examiner* — Karl J Puttlitz
(74) *Attorney, Agent, or Firm* — Baker & Hostetler LLP

(57) ABSTRACT

The invention provides new polymorphs of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride, pharmaceutical compositions containing them and their use in therapy.

17 Claims, 5 Drawing Sheets

(56) References Cited

FOREIGN PATENT DOCUMENTS

Figure 1:
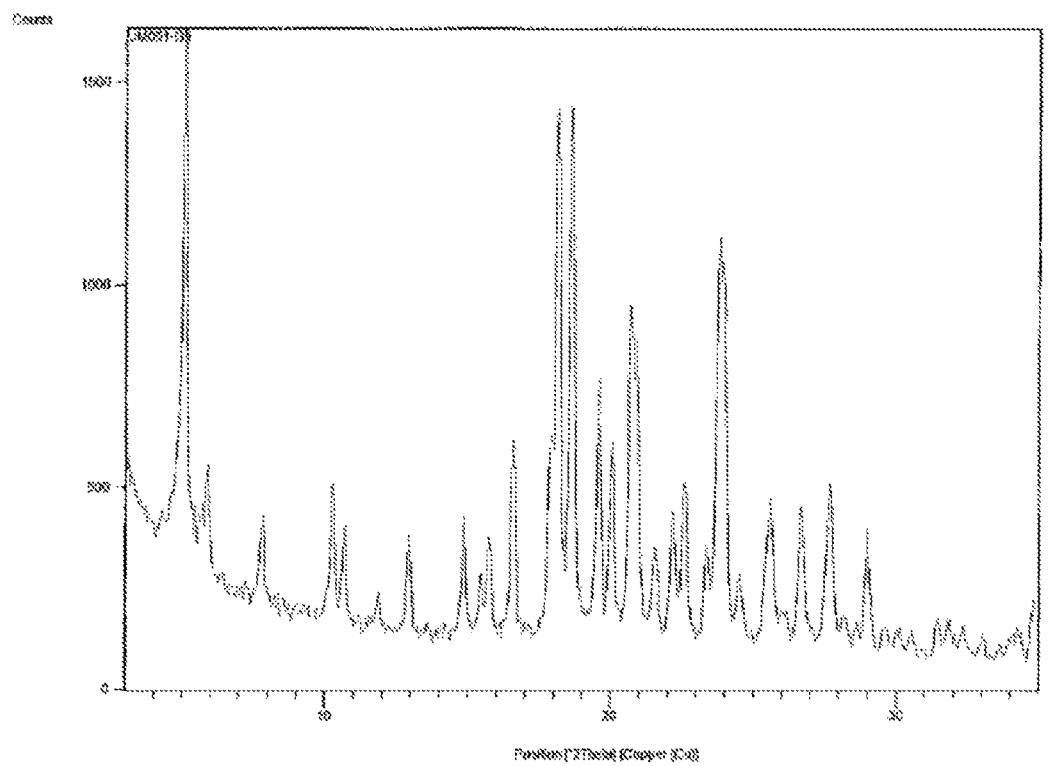

| | | |
|---|---|---|
| WO | WO 2008/049595 | 5/2008 |
| WO | WO 2011/075684 | 6/2011 |
| WO | WO 2011/094496 | 8/2011 |
| WO | WO 2011/118672 | 9/2011 |
| WO | WO 2012/004678 | 1/2012 |
| WO | WO 2012/017020 | 2/2012 |
| WO | WO 2012/142308 | 10/2012 |
| WO | 2013005045 * | 1/2013 |
| WO | WO 2013/005045 | 1/2013 |

OTHER PUBLICATIONS

Clermont et al., "Plasma Kallikrein Mediates Retinal Vascular Dysfunction and Induces Retinal Thickening in Diabetic Rats", Diabetes, May 2011, 60, 1590-1598.

Evans et al., "Selective Inhibitors of Plasma Kallikrein", Immunolpharmocology, 1996, 32, 115-116.

Garrett et al., "Peptide Aldehyde Inhibitors of the Kallikreins: An Investigation of Subsite Interactions With Tripeptides Containing Structural Variations at the Amino Terminus", J. Peptide Res., 1998, 52, 62-71.

Griesbacher et al., "Involvement of Tissue Kallikrein But Not Plsma Kallikrein in the Development of Symptoms Mediated by Endogenous Kinins in Acute Pancreatitus in Rats", British Journal of Pharmacology, 2002, 137, 692-700.

Kolte et al., "Biochemical Characterization of a Novel High-Affinity and Specific Plasma Kallikrein Inhibitor", British Journal of Pharmacology, Nov. 25, 2010, 162, 1639-1649.

Lehmann, "Ecallantide (DX-88), a Plasma Kallikrein Inhibitor for the Treatment of Hereditary Angioedema and the Prevention of Blood Loss in on-Pump Cardiothoracic Surgery", Expert Opinion Biol. Ther., Aug. 2008, 8, 1187-1199.

Marceau et al., "Bradykinin receptor Ligands: Therapeutic Perspectives", Nature Review, Drug Discovery 2004, Oct. 2004, vol. 3, 845-852.

Okada et al., "Development of Potent and Selective Plasmin and Plasma Kallikrein Inhibitors and Studies on the Structure-Activity Relationship", Chem. Pharm. Bull., 2000, 48, 12, 1964-1972.

Stürzbecher et al., "Novel Plasma Kallikrein Inhibitors of the Benzamidine Type", Brazilian J. med. Biol. Res., 1994, 27, 1929-1934.

Teno et al., "Development of Active Center-Directed Plasmin and Plasma Kallikrein Inhibitors and Studies on the Structure-Inhibitory Activity Relationship", Chem. Pharm. Bull., Jun. 1993, 41, 1079-1090.

Young et al., "Small Molecule Inhibitors of Plasma Kallikrein", Bioorg. Med. Chem. Letts., Apr. 2006, 16, 7, 2034-2036.

Zhang et al., "Discovery of Highly Potent Small Molecule Kallikrein Inhibitors", Medicinal Chemistry 2, 2006, 545-553.

* cited by examiner

POLYMORPHS OF N-[(R)-1-[(S)-1-(4-AMINOMETHYL-BENZYLCARBAMOYL)-2-PHENYL-ETHYLCARBAMOYL]-2-(4-ETHOXY-PHENYL)-ETHYL]-BENZAMIDE HYDROCHLORIDE

CROSS-REFERENCE TO RELATED APPLICATIONS

This application is the National Stage of International Patent Application No. PCT/GB2013/051781 filed Jul. 5, 2013, which claims the benefit of U.S. Provisional Patent Application No. 61/668,543, filed Jul. 6, 2012; and Great Britain Patent Application No. 1212081.2, filed Jul. 6, 2012, the disclosures of which are incorporated herein by reference in their entireties.

The present invention relates to new polymorphs of a plasma kallikrein inhibitor, a pharmaceutical composition containing them and their use in therapy.

BACKGROUND TO THE INVENTION

Inhibitors of plasma kallikrein have a number of therapeutic applications, particularly in the treatment of retinal vascular permeability associated with diabetic retinopathy and diabetic macular oedema. Other complications of diabetes such as cerebral haemorrhage, nepropathy, cardiomyopathy and neuropathy, all of which have associations with plasma kallikrein may also be considered as targets for a plasma kallikrein inhibitor.

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" *Cardiovascular and haematological agents in medicinal chemistry*, 7, p 234-250, 2009; K. D. Bhoola et al., *Pharmacological Rev.*, 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein. Kinins are potent mediators of inflammation that act through G protein-coupled receptors and antagonists of kinins (such as bradykinin antagonists) have previously been investigated as potential therapeutic agents for the treatment of a number of disorders (F. Marceau and D. Regoli, Nature Rev., Drug Discovery, 2004, 3, 845-852).

Kinins play a pivotal role in the pathogenesis of pancreatitis and may also be important in the progression of oedematous to necrotising forms of the disease. In animal models of pancreatitis pre-treatment with bradykinin antagonists has been shown to prevent oedema formation and sequelae such as hypotension, hypovalemia, haemoconcentration and accumulation of activated digestive enzymes within the pancreatic tissue (T. Griesbacher and F. Lembeck F. *Br. J. Pharmacol.*, 1992 107, 356-360; T. Griesbacher et al., *Br. J. Pharmacol.*, 1993, 108, 405-411). However, further development of bradykinin antagonists is limited by their lack of specificity and efficacy. Furthermore, it (T. Griesbacher et al., *Br. J. Pharmacol.*, 2003, 139, 299-308) has been shown that bradykinin antagonists increase levels of hK1 in the pancreas, indicating that treatment with hK1 inhibitors could be significantly more effective than bradykinin antagonists. Prevention of kinin formation through inhibition of hK1 thus represents a viable alternative to kinin antagonists for treatment of these disorders.

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastrointestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, p 1187-99).

The plasma kallikrein-kinin system is abnormally abundant in patients with advanced diabetic macular oedema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" *Diabetes*, 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular oedema.

Synthetic and small molecule plasma kallikrein inhibitors have been described previously, for example by Garrett et al. ("Peptide aldehyde . . . " *J. Peptide Res.* 52, p 62-71 (1998)), T. Griesbacher et al. ("Involvement of tissue kallikrein but not plasma kallikrein in the development of symptoms mediated by endogenous kinins in acute pancreatitus in rats" *British Journal of Pharmacology* 137, p 692-700 (2002)), Evans ("Selective dipeptide inhibitors of kallikrein" WO03/076458), Szelke et al. ("Kininogenase inhibitors" WO92/04371), D. M. Evans et al. (*Immunolpharmacology*, 32, p 115-116 (1996)), Szelke et al. ("Kininogen inhibitors" WO95/07921), Antonsson et al. ("New peptides derivatives" WO94/29335), J. Stürzbecher et al. (*Brazilian J. Med. Biol. Res* 27, p 1929-34 (1994)), Kettner et al. (U.S. Pat. No. 5,187,157), N. Teno et al. (*Chem. Pharm. Bull.* 41, p 1079-1090 (1993)), W. B. Young et al. ("Small molecule inhibitors of plasma kallikrein" *Bioorg. Med. Chem. Letts.* 16, p 2034-2036 (2006)), Okada et al. ("Development of potent and selective plasmin and plasma kallikrein inhibitors and studies on the structure-activity relationship" *Chem. Pharm. Bull.* 48, p 1964-72 (2000)), Steinmetzer et al. ("Trypsin-like serine protease inhibitors and their preparation and use" WO08/049595), Zhang et al. ("Discovery of highly potent small molecule kallikrein inhibitors" *Medicinal Chemistry* 2, p 545-553 (2006)), Sinha et al. ("Inhibitors of plasma kallikrein" WO08/016883), and Brandl et al. ("N-((6-amino-pyridin-3-yl)methyl)-heteroaryl-carboxamides as inhibitors of plasma kallikrein" WO2012/017020).

To date, no small molecule synthetic plasma kallikrein inhibitor has been approved for medical use. The molecules described in the known art suffer from limitations such as poor selectivity over related enzymes such as KLK1, thrombin and other serine proteases, and poor oral availability. The large protein kallikrein inhibitors present risks of anaphylactic reactions, as has been reported for Ecallantide. Thus there remains a need for compounds that selectively inhibit plasma kallikrein, that do not induce anaphylaxis and that are orally available. Furthermore, the majority of the molecules in the known art feature a highly polar and ionisable guanidine or amidine functionality. It is well known that such functionalities may be limiting to gut permeability and therefore to oral availability.

In the manufacture of pharmaceutical formulations, it is important that the active compound be in a form in which it can be conveniently handled and processed in order to obtain a commercially viable manufacturing process. Accordingly, the chemical stability and the physical stability of the active compound are important factors. The active compound, and formulations containing it, must be capable of being effectively stored over appreciable periods of time, without exhibiting any significant change in the physico-chemical characteristics (e.g. chemical composition, density, hygroscopicity and solubility) of the active compound.

It is known that manufacturing a particular solid-state form of a pharmaceutical ingredient can affect many aspects of its solid state properties and offer advantages in aspects of solubility, dissolution rate, chemical stability, mechanical properties, technical feasibility, processability, pharmacokinetics and bioavailability. Some of these are described in "Handbook of Pharmaceutical Salts; Properties, Selection and Use", P. Heinrich Stahl, Camille G. Wermuth (Eds.) (Verlag Helvetica Chimica Acta, Zurich). Methods of manufacturing solid-state forms are also described in "Practical Process Research and Development", Neal G. Anderson (Academic Press, San Diego) and "Polymorphism: In the Pharmaceutical Industry", Rolf Hilfiker (Ed) (Wiley VCH). Polymorphism in pharmaceutical crystals is described in Byrn (Byrn, S. R., Pfeiffer, R. R., Stowell, J. G., "Solid-State Chemistry of Drugs", SSCI Inc., West Lafayette, Ind., 1999), Brittain, H. G., "Polymorphism in Pharmaceutical Solids", Marcel Dekker, Inc., New York, Basel, 1999) or Bernstein (Bernstein, J., "Polymorphism in Molecular Crystals", Oxford University Press, 2002).

The applicant has developed a novel series of benzylamine derivatives that are inhibitors of plasma kallikrein, which are disclosed in WO2013/005045 (PCT/GB2012/051588). These compounds demonstrate good selectivity for plasma kallikrein and are potentially useful in the treatment of impaired visual acuity, diabetic retinopathy, macular oedema, hereditary angioedema, diabetes, pancreatitus, cerebral haemorrhage, nepropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post-operative surgery. One such benzylamine derivative is N—[(R)-1-[(S)-1-(4-aminomethyl-benzylcarbamoyl)-2-phenyl-ethylcarbamoyl]-2-(4-ethoxy-phenyl)-ethyl]-benzamide. Initial attempts to prepare N—[(R)-1-[(S)-1-(4-aminomethyl-benzylcarbamoyl)-2-phenyl-ethylcarbamoyl]-2-(4-ethoxy-phenyl)-ethyl]-benzamide yielded an amorphous solid. However, the applicant has now developed novel, stable crystalline forms of the hydrochloric acid salt of this compound, which are herein referred to as 'Form 1' and 'Form 2'. The novel solid forms have advantageous physico-chemical properties that render them suitable for development.

Figure 4:
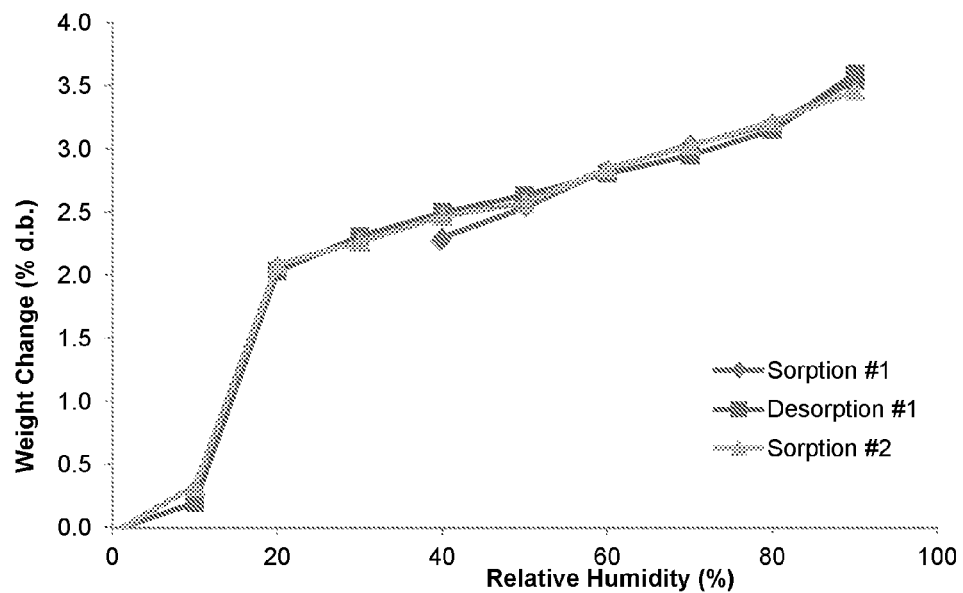

For example, Gravimetric Vapour Sorption (GVS) data of "Form 1" of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride, FIG. 4, show that hydration is reversible (i.e. no significant hysteresis). Furthermore, these data show that under normal conditions (20% to 80% relative humidity) there is only a relatively gradual increase in water content. This may be due to sample wetting and is consistent with the absence of significant hygroscopicity.

Further evidence of the suitability of the crystalline forms for pharmaceutical development is provided by the following stability data. Form 1 of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride was packed into double polyethylene bags within a polypropylene container and stored at 40° C. and 75% relative humidity for 6 months:—

There was no change to the XRPD diffractogram

The water content (using the Karl Fischer test method) initially increased immediately after preparation, which included a drying operation, but stabilised to a range approximately 2.5%-2.8% w/w after one month and remained within this range thereafter. These data are consistent with the GVS data and further demonstrate the absence of significant hygroscopicity There was no significant chemical degradation. The purity (HPLC) remained at 99.8% area

DESCRIPTION OF THE INVENTION

Thus, in accordance with an aspect of the present invention, there is provided crystalline polymorphs of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride. In the present application these polymorphs may be referred to as 'Form 1' and 'Form 2'.

The name N—[(R)-1-[(S)-1-(4-aminomethyl-benzylcarbamoyl)-2-phenyl-ethylcarbamoyl]-2-(4-ethoxy-phenyl)-ethyl]-benzamide denotes the structure depicted in Figure A.

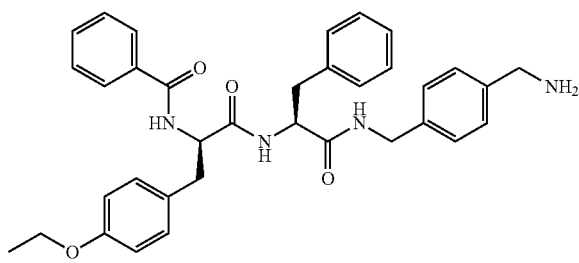

FIG. A

The present invention encompasses solvates (e.g. hydrates) of the crystalline forms of N-[(R)-1-[(S)-1-(4-aminomethyl-benzylcarbamoyl)-2-phenyl-ethylcarbamoyl]-2-(4-ethoxy-phenyl)-ethyl]-benzamide hydrochloride.

Two crystalline polymorphs of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride have been isolated and characterised to date, which are herein referred to as 'Form 1' and 'Form 2'.

In a preferred aspect the crystalline form is Form 1. In an aspect of the invention, the crystalline form of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride is a hydrate, particularly a monohydrate or hemihydrate.

In the present specification, X-ray powder diffraction peaks (expressed in degrees 2θ) are measured using Cu Kα radiation.

The present invention provides a crystalline form (Form 1) of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride, which exhibits at least the following characteristic X-ray powder diffraction peaks (Cu Kα radiation, expressed in degrees 2θ) at approximately:
(1) 5.1, 10.3, 10.7, 18.1 and 18.6; or
(2) 5.1, 10.3, 10.7, 14.9, 17.9, 18.1 and 18.6; or
(3) 5.1, 7.8, 10.3, 10.7, 14.9, 16.6, 17.9, 18.1 and 18.6.

The term "approximately" means in this context that there is an uncertainty in the measurements of the degrees 2θ of ±0.2 (expressed in degrees 2θ).

The present invention also provides a crystalline form (Form 1) of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride, having an X-ray powder diffraction pattern comprising characteristic peaks (expressed in degrees 2θ) at approximately 5.1, 7.8, 10.3, 10.7, 13.0, 14.9, 16.6, 17.9, 18.1 and 18.6.

The present invention also provides a crystalline form (Form 1) of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride, having an X-ray powder diffraction pattern which exhibits at least the following characteristic d-space values (Å) of approximately:
(1) 17.32, 8.61, 8.23, 4.89 and 4.76; or
(2) 17.32, 8.61, 8.23, 5.96, 4.97, 4.89 and 4.76; or
(3) 17.32, 11.28, 8.61, 8.23, 5.96, 5.34, 4.97, 4.89 and 4.76.

The term "approximately" means in this context that there is an uncertainty in the measurements of the d-space values (Å) of ±0.2 (expressed in Å).

FIG. 1 shows an X-ray powder diffraction pattern of Form 1 of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride. The present invention also provides a provides a crystalline form (Form 1) of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride having an X-ray powder diffraction pattern substantially the same as that shown in FIG. 1.

Figure 2:
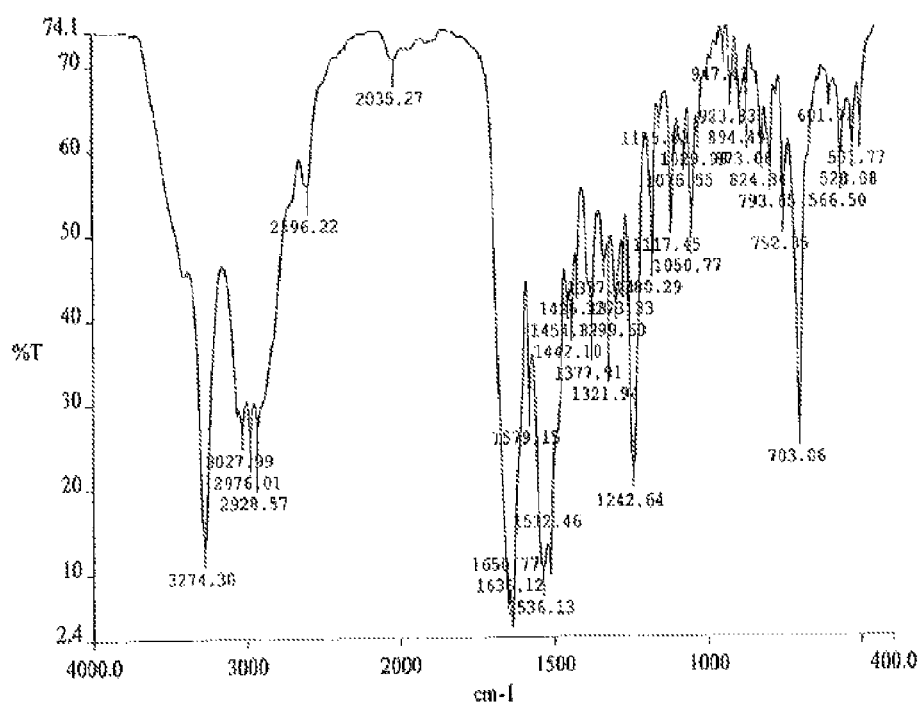

FIG. 2 shows an IR spectrum of Form 1 of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride. The present invention also provides a provides a crystalline form (Form 1) of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride which is characterised by an IR spectrum having characteristic peaks expressed in cm$^{-1}$ at approximately 3274, 3027, 2976, 2928, 1651, 1636, 1536, 1512, 1243 and 703.

The term "approximately" means in this context that the cm$^{-1}$ values can vary, e.g. by up to ±1 cm$^{-1}$. Additionally, the present invention provides a crystalline form (Form 1) of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride having an IR spectrum substantially the same as that shown in FIG. 2.

The present invention also provides a crystalline form (Form 2) of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride, which exhibits at least the following characteristic X-ray powder diffraction peaks (Cu Kα radiation, expressed in degrees 2θ) at approximately:
(1) 3.3, 5.7, 18.6, 24.4, 25.5; or
(2) 3.3, 5.7, 6.7, 18.6, 24.4, 25.5; or
(3) 3.3, 5.7, 6.7, 8.3, 11.0, 18.6, 24.4, 25.5;

The present invention also provides a crystalline form (Form 2) of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride, having an X-ray powder diffraction pattern comprising characteristic peaks (expressed in degrees 2θ) at approximately 3.3, 4.7, 5.7, 6.0, 6.7, 8.3, 11.0, 18.6, 24.4, 25.5.

The present invention also provides a crystalline form (Form 2) of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride, having an X-ray powder diffraction pattern which exhibits at least the following characteristic d-space values (Å) of approximately:
(1) 26.72, 15.52, 4.77, 3.65, 3.49; or
(2) 26.72, 15.52, 13.26, 4.77, 3.65, 3.49; or
(3) 26.72, 15.52, 13.26, 10.66, 8.04, 4.77, 3.65, 3.49.

Figure 5:
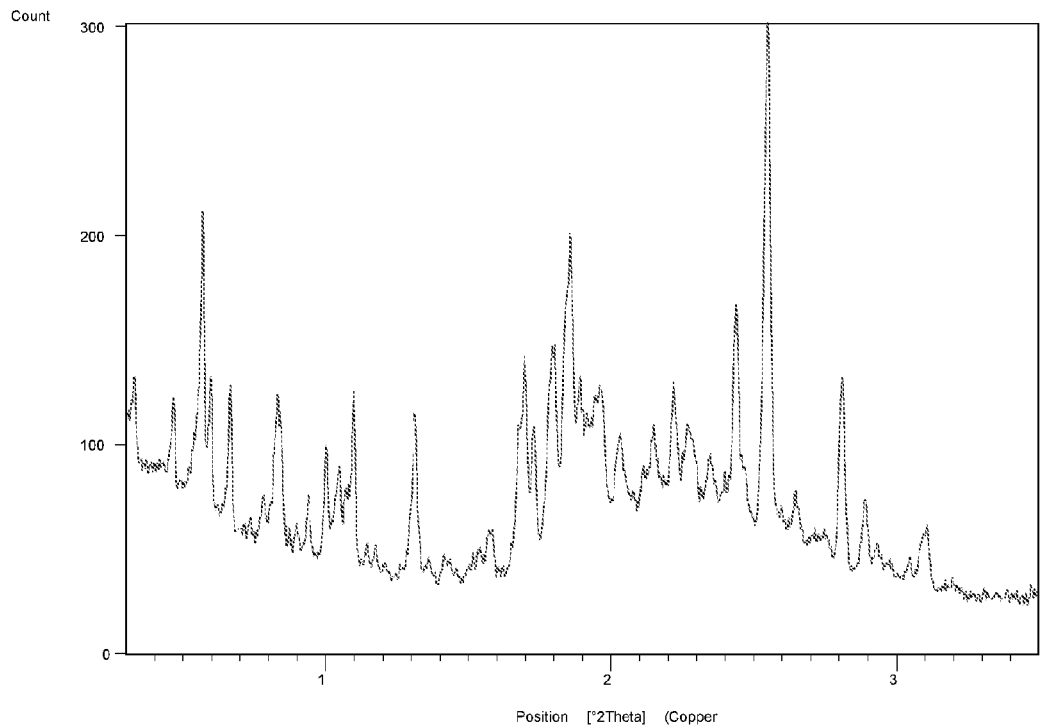

FIG. 5 shows an X-ray powder diffraction pattern of Form 2 of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride. The present invention also provides a provides a crystalline form (Form 2) of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride having an X-ray powder diffraction pattern substantially the same as that shown in FIG. 5.

The crystalline form of the present invention can exist in both unsolvated and solvated forms. The term 'solvate' is used herein to describe a molecular complex comprising the compound of the invention and an amount of one or more pharmaceutically acceptable solvents, for example, ethanol. The term 'hydrate' is employed when the solvent is water.

The present invention also encompasses a process for the preparation of Form 1 of the present invention, said process comprising the crystallisation of said crystalline form from a solution of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride in a solvent or a mixture of solvents. In an aspect of the invention, the solvent mixture is acetonitrile and water. In another aspect the solvent mixture is acetonitrile and dimethylsulfoxide. In another aspect, N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride is added to a solvent or a mixture of solvents (e.g. acetonitrile and water or acetonitrile and dimethylsulfoxide) and the combined mixture (compound plus solvent(s)) heated to a temperature of approximately 70-85° C. before being allowed to cool to room temperature. Alternatively, in this aspect, the combined mixture is heated to a temperature of approximately 75-80° C. before being allowed to cool to room temperature. Alternatively, in this aspect, the combined mixture is heated to a temperature of approximately 75, 76, 77, 78, 79 or 80° C. before being allowed to cool to room temperature. Alternatively, in this aspect, the combined mixture is heated to a temperature of approximately 77° C. before being allowed to cool to room temperature.

Alternatively, the said crystalline form may be obtained by thermal cycling of the solid amorphous form (e.g. heat/cool cycling the sample via differential scanning calorimetry up to 245°).

The processes of the present invention may also comprise the addition of crystalline seeds of the crystalline form of the invention.

In an aspect, the present invention provides the crystalline form of the invention when manufactured by a process according to the invention.

As previously mentioned, the crystalline form of the present invention has a number of therapeutic applications, particularly in the treatment of diseases or conditions mediated by plasma kallikrein.

Accordingly, the present invention provides a crystalline form of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride, as hereinbefore defined, for use in therapy. In a preferred embodiment, the crystalline form is Form 1.

The present invention also provides for the use of a crystalline form of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride, as hereinbefore defined, in the manufacture of a medicament for the treatment of a disease or condition mediated by plasma kallikrein. In a preferred embodiment, the crystalline form is Form 1.

The present invention also provides a crystalline form of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride, as hereinbefore defined, for use in a method of treatment of a disease or condition mediated by plasma kallikrein. In a preferred embodiment, the crystalline form is Form 1.

The present invention also provides a method of treatment of a disease or condition mediated by plasma kallikrein, said method comprising administering to a mammal in need of such treatment a therapeutically effective amount of a crystalline form of N-[(R)-1-[(S)-1-(4-aminomethyl-benzylcarbamoyl)-2-phenyl-ethylcarbamoyl]-2-(4-ethoxy-phenyl)-ethyl]-benzamide hydrochloride, as hereinbefore defined. In a preferred embodiment, the crystalline form is Form 1.

In an aspect, the disease or condition mediated by plasma kallikrein is selected from impaired visual acuity, diabetic retinopathy, diabetic macular oedema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post-operative surgery.

In an aspect, the disease or condition mediated by plasma kallikrein is retinal vascular permeability associated with diabetic retinopathy or diabetic macular oedema.

In the context of the present invention, references herein to "treatment" include references to curative, palliative and prophylactic treatment, unless there are specific indications to the contrary. The terms "therapy, "therapeutic" and "therapeutically" should be construed in the same way.

The crystalline form of the present invention may be administered alone or in combination with one or more other drugs. Generally, it will be administered as a formulation in association with one or more pharmaceutically acceptable excipients. The term "excipient" is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

In another aspect, the compounds of the present invention may be administered in combination with laser treatment of the retina. The combination of laser therapy with intravitreal injection of an inhibitor of VEGF for the treatment of diabetic macular edema is known (Elman M, Aiello L, Beck R, et al. "Randomized trial evaluating ranibizumab plus prompt or deferred laser or triamcinolone plus prompt laser for diabetic macular edema". Ophthalmology. 27 Apr. 2010).

Pharmaceutical compositions suitable for the delivery of the crystalline form of the present invention and methods for their preparation will be readily apparent to those skilled in the art. Such compositions and methods for their preparation may be found, for example, in Remington's Pharmaceutical Sciences, 19th Edition (Mack Publishing Company, 1995).

For administration to human patients, the total daily dose of the crystalline form of the invention is typically in the range 0.01 mg and 1000 mg, or between 0.1 mg and 250 mg, or between 1 mg and 50 mg depending, of course, on the mode of administration. If administered by intra-vitreal injection a lower dose of between 0.0001 mg (0.1 μg) and 0.2 mg (200 μg) per eye is envisaged, or between 0.0005 mg (0.5 μg) and 0.05 mg (50 μg) per eye.

The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Accordingly, the present invention provides a pharmaceutical composition comprising a crystalline solid form of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride, as hereinbefore defined, and a pharmaceutically acceptable carrier, diluent or excipient. In a preferred embodiment, the crystalline solid form is Form 1.

The pharmaceutical compositions may be administered topically (e.g. to the eye, to the skin or to the lung and/or airways) in the form, e.g., of eye-drops, creams, solutions, suspensions, heptafluoroalkane (HFA) aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

In an embodiment of the invention, the active ingredient is administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the crystalline form in an immediate release manner or in a rate-sustaining manner, wherein the release profile can be delayed, pulsed, controlled, sustained, or delayed and sustained or modified in such a manner which optimises the therapeutic efficacy of the said crystalline form. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, suspensions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The crystalline form of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

The invention will now be illustrated by the following non-limiting examples. In the examples the following figures are presented:

FIG. 1: X-ray powder diffraction pattern of Form 1 of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride.

FIG. 2: IR spectrum of Form 1 of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride.

Figure 3:
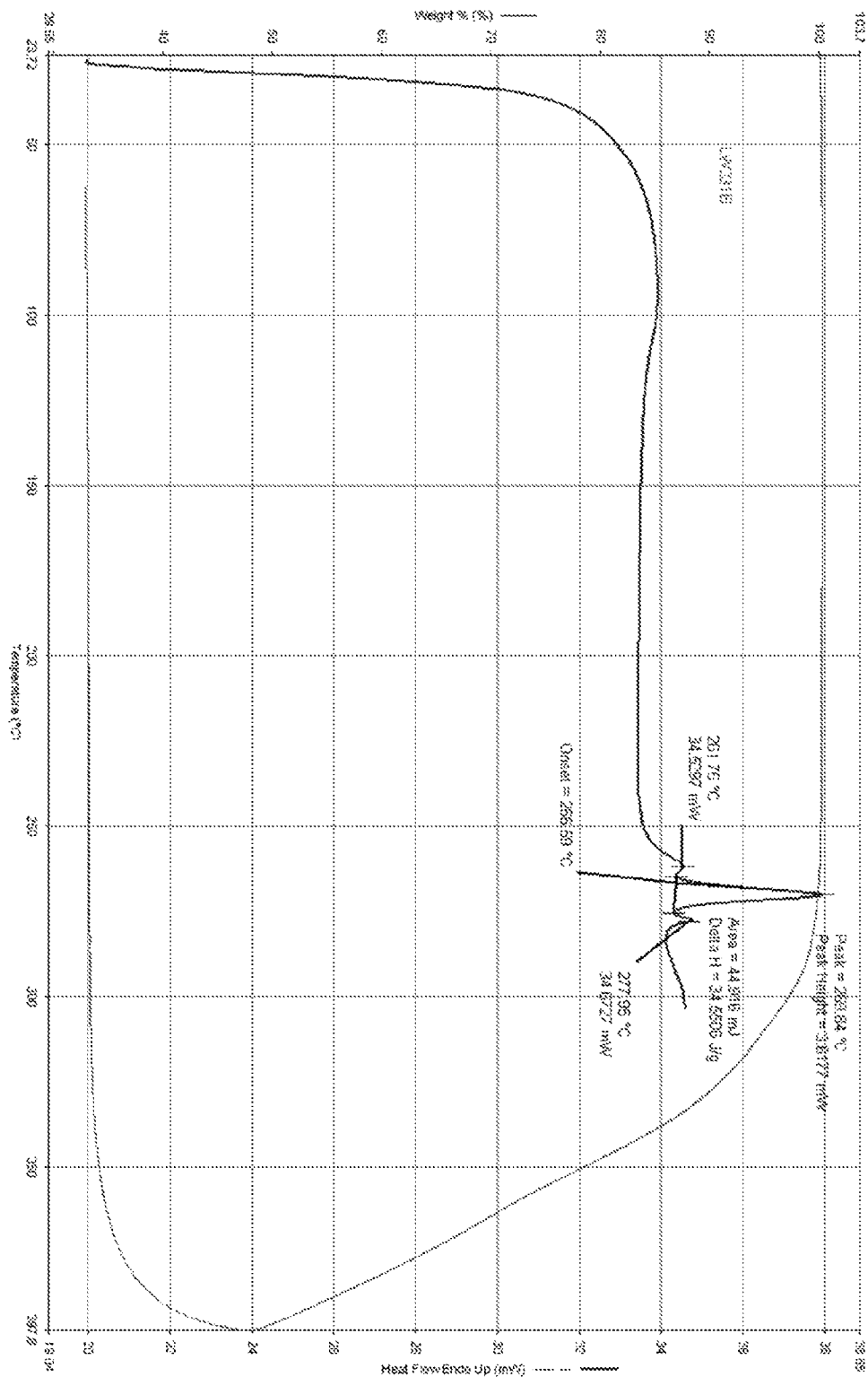

FIG. 3: DSC thermograph of Form 1 of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride.

FIG. 4: Gravimetric vapour sorption isotherms (sorption, desorption and sorption) of Form 1 of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride.

FIG. 5: X-ray powder diffraction pattern of Form 2 of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride.

Figure 6:
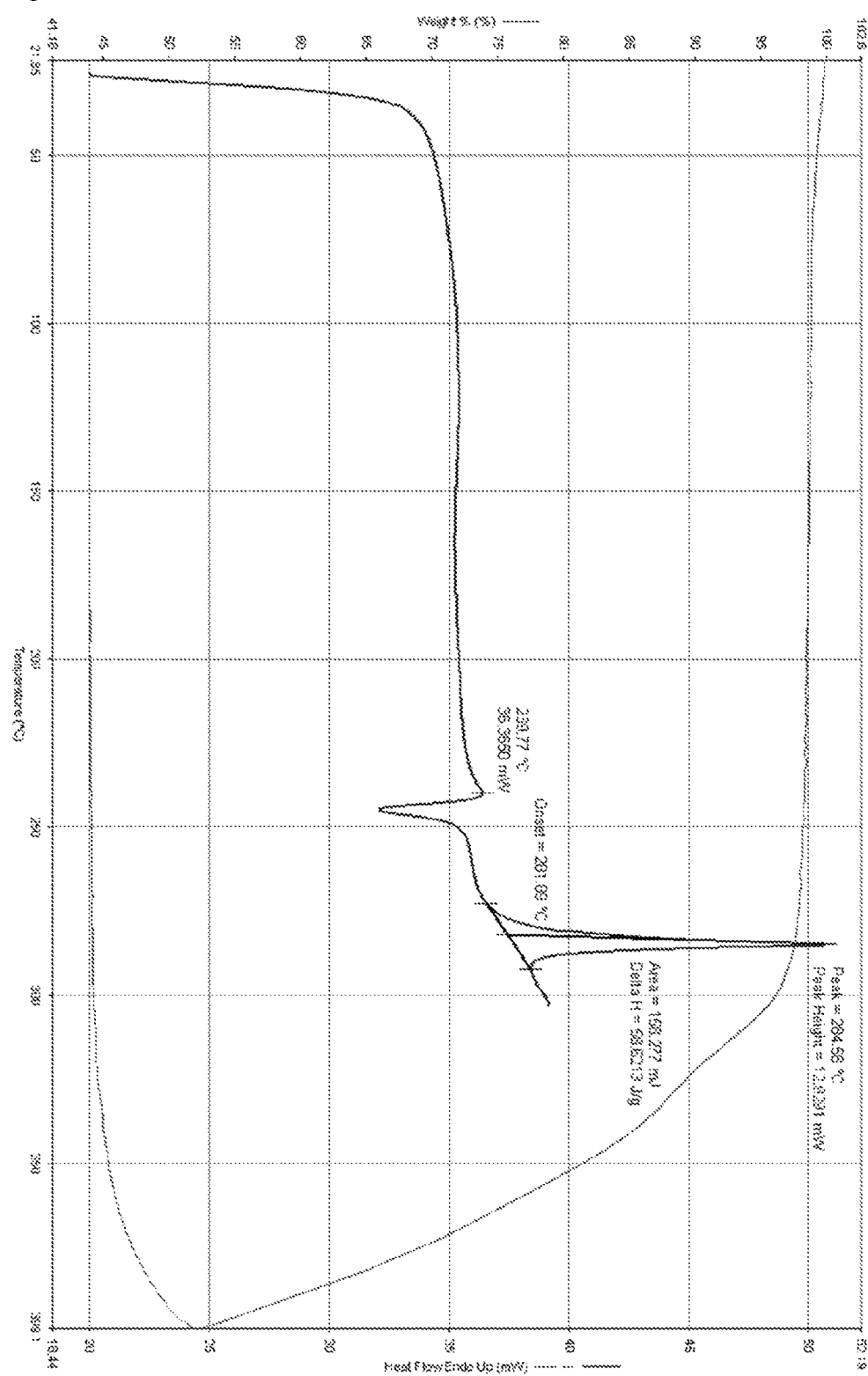

FIG. 6: DSC thermograph of Form 2 of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride.

Figure 7:
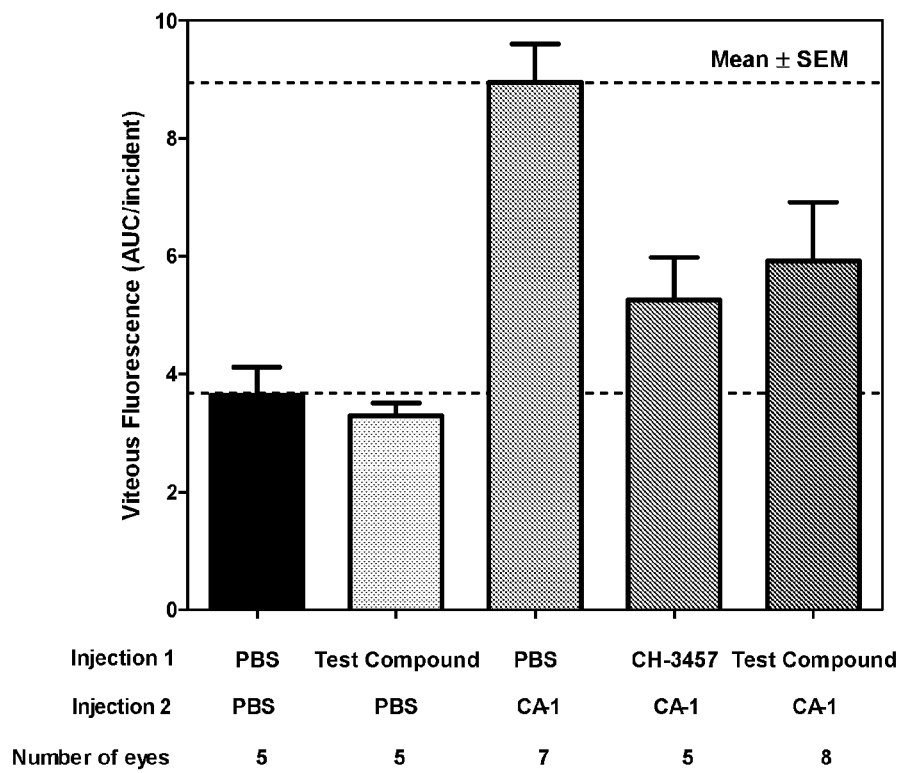

FIG. 7: Shows the inhibitory effect of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (labelled as "Test Compound") and CH-3457 (positive control; plasma kallikrein inhibitor) upon CA-I stimulated RVP in Sprague Dawley rats.

Figure 8:
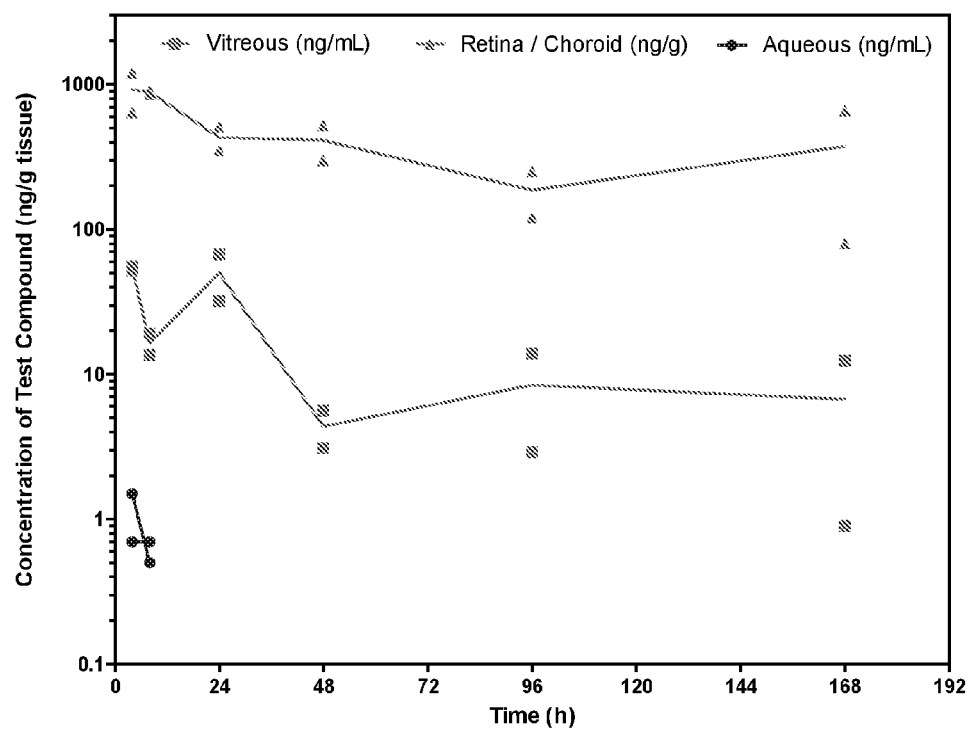

FIG. 8: Shows the ocular tissue concentrations of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (labelled as "Test Compound") following IVT administration of 4.2 µg/mL (210 ng/eye).

GENERAL EXPERIMENTAL DETAILS $^1$H NMR spectra were recorded on a Brucker Avance III (400 MHz) spectrometer with reference to deuterium solvent and at room temperature.

Molecular ions were obtained using LCMS which was carried out using a Chromolith Speedrod RP-18e column, 50×4.6 mm, with a linear gradient 10% to 90% 0.1% $HCO_2H$/MeCN into 0.1% $HCO_2H/H_2O$ over 11 min, flow rate 1.5 mL/min. Data was collected using a Thermofinnigan Surveyor MSQ mass spectrometer with electrospray ionisation in conjunction with a Thermofinnigan Surveyor LC system.

Chemical names were generated using the Autonom software provided as part of the ISIS draw package from MDL Information Systems.

All solvents and commercial reagents were used as received.

Infra-red spectra were measured using a system set to a standard absorbance configuration, with samples prepared with potassium bromide, and scanned from 4000 $cm^{-1}$ to 400 $cm^{-1}$.

X-Ray Powder Diffraction patterns were collected on a PANalytical diffractometer using Cu Kα radiation (45 kV, 40 mA), θ-θ goniometer, focusing mirror, divergence slit (½"), soller slits at both incident and divergent beam (4 mm) and a PIXcel detector. The software used for data collection was X'Pert Data Collector, version 2.2f and the data was presented using X'Pert Data Viewer, version 1.2d.

XRPD patterns were acquired under ambient conditions via a transmission foil sample stage (polyimide—Kapton, 12.7 µm thickness film) under ambient conditions using a PANalytical X'Pert PRO. The data collection range was 2.994-35° 2θ with a continuous scan speed of 0.202004° $s^{-1}$.

DSC data were collected on a PerkinElmer Pyris 4000 DSC equipped with a 45 position sample holder. The instrument was verified for energy and temperature calibration using certified indium. A predefined amount of the sample, 0.5-3.0 mg, was placed in a pin holed aluminium pan and heated at 20° C. min-1 from 30 to 350° C., or varied as experimentation dictated. A purge of dry nitrogen at 60 ml·min-1 was maintained over the sample. The instrument control, data acquisition and analysis was performed with Pyris Software v9.0.1.0203.

N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (Form 1)

Method

A. {(S)-1-[4-(tert-Butoxycarbonylamino-methyl)-benzylcarbamoyl]-2-phenyl-ethyl}-carbamic acid benzyl ester (S)-2-Benzyloxycarbonylamino-3-phenyl-propionic acid 2,5-dioxo-pyrrolidin-1-yl ester (4.25 g, 10.72 mmol) was dissolved in $CH_2Cl_2$ (100 mL). This solution was cooled to 0° C. 1-(N-Boc-Aminomethyl)-4-(aminomethyl)benzene (2.79 g, 11.79 mmol) was added followed by triethylamine (3.25 g, 32.16 mmol). After 18 hrs at 0° C. to room temperature reaction mixture was diluted with chloroform (100 mL) and washed with $NaHCO_3$ (1×30 mL), water (1×30 mL), brine (1×30 mL), dried ($Na_2SO_4$) evaporated in vacuo giving a yellow oil. The residue was triturated with Pet. Ether (60-80° C.) and EtOAc to give a white solid identified as {(S)-1-[4-(tert-butoxycarbonylamino-methyl)-benzylcarbamoyl]-2-phenyl-ethyl}-carbamic acid benzyl ester (3.88 g, 7.49 mmol, 70%).

[M+H]$^+$=518.28, 540.32 (M+Na).

B. {4-[((S)-2-Amino-3-phenyl-propionylamino)-methyl]-benzyl}-carbamic acid tert-butyl ester {(S)-1-[4-(tert-Butoxycarbonylamino-methyl)-benzylcarbamoyl]-2-phenyl-ethyl}-carb amic acid benzyl ester (3.66 g, 7.08 mmol) was dissolved in methanol (200 mL). This solution was hydrogenated over 10% Pd/C (500 mg) at atmospheric pressure and room temperature for one hour after which time the catalyst was filtered off through celite and the residue washed with methanol (30 mL), the combined filtrates were evaporated in vacuo to give a white solid identified as {4-[((S)-2-amino-3-phenyl-propionylamino)-methyl]-benzyl}-carbamic acid tert-butyl ester (2.627 g, 6.85 mmol, 97%).

[M+H]+=384.37

C. (R)-2-Amino-3-(4-ethoxy-phenyl)-propionic acid (R)-2-Butoxycarbonylamino-3-(4-ethoxy-phenyl)-propionic acid (4.0 g, 12.93 mmol) was dissolved in 4M HCl in dioxan (150 mL). After one hour at room temperature the solvent was removed in vacuo to give a white solid identified as (R)-2-amino-3-(4-ethoxy-phenyl)-propionic acid hydrochloride (3.18 g, 12.9 mmol, 100%).

[M+H]$^+$=210.18

D. (R)-2-Benzyloxycarbonylamino-3-(4-ethoxy-phenyl)-propionic acid (R)-2-Amino-3-(4-ethoxy-phenyl)-propionic acid hydrochloride (3.17 g, 12.9 mmol) was dissolved in a solution of sodium hydroxide (1.14 g, 28.38 mmol) in water (100 mL). Benzyl chloroformate (2.64 g, 15.48 mmol) in dioxan (100 mL) was added. The reaction mixture was stirred at room temperature for 18 hrs after which time the dioxan was removed in vacuo. The aqueous residue was washed with diethyl ether (1×100 mL), acidified to pH 2 with 1M HCl and extracted with chloroform (2×200 mL). The combined extracts were washed with water (1×50 mL), brine (1×50 mL), dried (Na$_2$SO$_4$) and evaporated in vacuo to give a white solid identified as (R)-2-benzyloxycarbonylamino-3-(4-ethoxy-phenyl)-propionic acid (4.0 g, 11.65 mmol, 90%).

[M+H]$^+$=344.20.

E. [(R)-1-{(S)-1-[4-(tert-Butoxycarbonylamino-methyl)-benzylcarbamoyl]-2-phenyl-ethylcarbamoyl}-2-(4-ethoxy-phenyl)-ethyl]-carbamic acid benzyl ester {4-[((S)-2-Amino-3-phenyl-propionylamino)-methyl]-benzyl}-carbamic acid tert-butyl ester (2.63 g, 6.86 mmol) was dissolved in CH$_2$Cl$_2$ (100 mL) and DMF (5 mL). This solution was cooled to 0° C. (R)-2-Benzyloxycarbonylamino-3-(4-ethoxy-phenyl)-propionic acid (2.59 g, 7.54 mmol) was added followed by HOBt (1.11 g, 8.23 mmol) and triethylamine (2.08 g, 20.57 mmol). Water soluble carbodiimide (1.45 g, 7.54 mmol) was then added. After 18 hrs at 0° C. to room temperature the reaction mixture was diluted with chloroform (200 mL) and washed with NaHCO$_3$ (1×50 mL), water (1×50 mL), brine (1×50 mL), dried (Na$_2$SO$_4$) and evaporated in vacuo giving a yellow oil. The residue was triturated with ethyl acetate and Pet. Ether (60-80° C.) to give a white solid identified as [(R)-1-{(S)-1-[4-(tert-butoxycarbonylamino-methyl)-benzylcarbamoyl]-2-phenyl-ethylcarbamoyl}-2-(4-ethoxy-phenyl)-ethyl]-carbamic acid benzyl ester (3.55 g, 5.01 mmol, 73%).

[M+H]$^+$=709.34.

F. [4-({(S)-2-[(R)-2-Amino-3-(4-ethoxy-phenyl)-propionylamino]-3-phenyl-propionylamino}-methyl)-benzyl]-carbamic acid tert-butyl ester

[(R)-1-{(S)-1-[4-(tert-Butoxycarbonylamino-methyl)-benzylcarbamoyl]-2-phenyl-ethylcarbamoyl}-2-(4-ethoxy-phenyl)-ethyl]-carbamic acid benzyl ester (3.55 g, 5.00 mmol) was dissolved in methanol (200 mL). This solution was hydrogenated over 10% Pd/C (500 mg) at atmospheric pressure and room temperature for one hour after which time the catalyst was filtered off through Celite and the residue washed with methanol (30 mL), the combined filtrates were evaporated in vacuo to give a white solid identified as [4-({(S)-2-[(R)-2-amino-3-(4-ethoxy-phenyl)-propionylamino]-3-phenyl-propionylamino}-methyl)-benzyl]-carbamic acid tert-butyl ester (2.8 g, 4.87 mmol, 97%).

[M+H]+=575.37.

G. [4-({(S)-2-[(R)-2-Benzoylamino-3-(4-ethoxy-phenyl)-propionylamino]-3-phenyl-propionylamino}-methyl)-benzyl]-carbamic acid tert-butyl ester

[4-({(S)-2-[(R)-2-Amino-3-(4-ethoxy-phenyl)-propionylamino]-3-phenyl-propionylamino}-methyl)-benzyl]-carbamic acid tert-butyl ester (3.45 g, 5.99 mmol) was dissolved in dichloromethane (150 mL). Benzoyl chloride (1.01 g, 7.19 mmol) was added followed by triethylamine (1.82 g, 17.98 mmol). The reaction mixture was stirred at room temperature for 5 hrs and diluted with CHCl$_3$ (150 mL), this solution was washed with 0.3M KHSO$_4$ (1×50 mL), sat. NaHCO$_3$ (1×50 mL), water (1×50 mL), brine (1×50 mL), dried (Na$_2$SO$_4$) and evaporated in vacuo. The residue was triturated with Pet Ether (60-80° C.) and EtOAc to give a white solid identified as [4-({(S)-2-[(R)-2-benzoylamino-3-(4-ethoxy-phenyl)-propionylamino]-3-phenyl-propionylamino}-methyl)-benzyl]-carbamic acid tert-butyl ester (3.06 g, 4.51 mmol, 75%).

[M+H]$^+$=679.34.

H. N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (Form 1)

[4-({(S)-2-[(R)-2-Benzoylamino-3-(4-ethoxy-phenyl)-propionylamino]-3-phenyl-propionylamino}-methyl)-benzyl]-carbamic acid tert-butyl ester (10.0 g, 14.7 mmol) was stirred in hydrogen chloride/ethyl acetate (3.7M, 250 mL) at room temperature. After two hours the mixture was filtered, washed with ethyl acetate (2×50 mL) and dried to afford a solid (7.9 g). A portion of the solid (0.106 g) was suspended in a mixture of acetonitrile (2.1 mL) and water (0.32 mL), stirred, and heated to 77° C. Additional aliquots of water (0.05 mL) were added successively to the mixture until dissolution was observed. The stirred mixture was then cooled to room temperature overnight. The resulting solid was isolated by filtration and dried in vacuo at 40° C. to afford N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (Form 1) (0.067 g, 3.41 mmol, 81%).

[M+H]$^+$=579.34

$^1$H NMR: (CD$_3$OD), 1.40 (3H, t, J=6.9 Hz), 2.91-2.99 (3H, m), 3.14-3.19 (1H, m), 4.02 (2H, q, J=6.9 Hz), 4.08 (2H, s), 4.41 (1H, d, J=15.5 Hz), 4.51 (1H, d, J=15.5 Hz), 4.66-4.69 (2H, m), 6.82 (2H, d, J=8.4 Hz), 7.10 (2H, d, J=8.2 Hz), 7.18-7.20 (2H, m), 7.25-7.38 (7H, m), 7.44-7.59 (3H, m), 7.72 (2H, d, J=7.8 Hz).

An XRPD diffractogram of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (Form 1) is shown in FIG. 1.

Peak position table:

| Pos. [°2Th.] | Height [cts] | FWHM [°2Th.] | d-spacing [Å] | Rel. Int. [%] |
|---|---|---|---|---|
| 5.1017 | 1329.67 | 0.1023 | 17.32212 | 100.00 |
| 5.9073 | 268.87 | 0.1023 | 14.96140 | 20.22 |
| 7.8360 | 212.97 | 0.1279 | 11.28276 | 16.02 |
| 10.2760 | 325.77 | 0.1279 | 8.60856 | 24.50 |
| 10.6870 | 227.90 | 0.1023 | 8.27835 | 17.14 |
| 11.8572 | 67.00 | 0.1535 | 7.46389 | 5.04 |
| 12.9566 | 230.78 | 0.1535 | 6.83291 | 17.36 |
| 14.8739 | 293.35 | 0.1279 | 5.95615 | 22.06 |
| 15.4578 | 148.51 | 0.1023 | 5.73245 | 11.17 |
| 15.7597 | 243.28 | 0.1535 | 5.62332 | 18.30 |
| 16.5908 | 488.41 | 0.1535 | 5.34347 | 36.73 |
| 17.8537 | 439.46 | 0.1279 | 4.96822 | 33.05 |
| 18.1443 | 1305.68 | 0.1535 | 4.88931 | 98.20 |
| 18.6294 | 1316.97 | 0.1535 | 4.76308 | 99.05 |
| 19.5704 | 643.93 | 0.1279 | 4.53612 | 48.43 |
| 20.0346 | 491.15 | 0.1791 | 4.43206 | 36.94 |
| 20.6761 | 789.56 | 0.1535 | 4.29598 | 59.38 |
| 20.9345 | 644.58 | 0.1279 | 4.24353 | 48.48 |
| 21.5959 | 208.07 | 0.2047 | 4.11503 | 15.65 |
| 22.1545 | 308.04 | 0.1791 | 4.01253 | 23.17 |
| 22.5745 | 392.23 | 0.1791 | 3.93883 | 29.50 |
| 23.3449 | 238.25 | 0.1279 | 3.81055 | 17.92 |
| 23.7157 | 786.12 | 0.1791 | 3.75181 | 59.12 |
| 23.9647 | 892.17 | 0.1535 | 3.71338 | 67.10 |
| 24.5150 | 156.93 | 0.2047 | 3.63125 | 11.80 |
| 25.5989 | 359.73 | 0.1791 | 3.47991 | 27.05 |
| 26.6668 | 341.96 | 0.2303 | 3.34294 | 25.72 |
| 27.6988 | 394.43 | 0.2047 | 3.22068 | 29.66 |
| 28.1867 | 71.81 | 0.1535 | 3.16604 | 5.40 |
| 28.9888 | 296.12 | 0.1279 | 3.08023 | 22.27 |
| 29.5799 | 56.04 | 0.2047 | 3.02001 | 4.21 |
| 30.5389 | 38.86 | 0.1535 | 2.92733 | 2.92 |
| 31.4200 | 71.21 | 0.1535 | 2.84722 | 5.36 |
| 31.8195 | 63.64 | 0.1535 | 2.81237 | 4.79 |
| 33.0388 | 37.25 | 0.1535 | 2.71132 | 2.80 |
| 34.1843 | 48.19 | 0.3070 | 2.62305 | 3.62 |
| 34.8271 | 94.43 | 0.2047 | 2.57609 | 7.10 |

Infra-Red Spectroscopy

The IR spectrum of Form 1 comprises peaks at wavelengths of approximately 3274, 3027, 2976, 2928, 1651, 1636, 1536, 1512, 1243 and 703 cm$^{-1}$. The spectrum is presented in FIG. 2.

Differential Scanning Calorimetry (DSC)

The DSC data for Form 1 are shown in FIG. 3.

Gravimetric Vapour Sorption

Sorption isotherms were obtained using a Hiden Isochema moisture sorption analyser (model IGAsorp), controlled by IGAsorp Systems Software V6.50.48. The sample was maintained at a constant temperature (25° C.) by the instrument controls. The humidity was controlled by mixing streams of dry and wet nitrogen, with a total flow of 250 ml·min-1. The instrument was verified for relative humidity content by measuring three calibrated Rotronic salt solutions (10-50-88%). The weight change of the sample was monitored as a function of humidity by a microbalance (accuracy +/−0.005 mg). A defined amount of sample was placed in a tared mesh stainless steel basket under ambient conditions. A full experimental cycle consisted of three scans (sorption, desorption and sorption) at a constant temperature (25° C.) and 10% RH intervals over a 0-90% range (60 minutes for each humidity level).

The GVS data for Form 1 are shown in FIG. 4.

N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (Form 2)

Method

[4-({(S)-2-[(R)-2-Benzoylamino-3-(4-ethoxy-phenyl)-propionyl amino]-3-phenyl-propionylamino}-methyl)-benzyl]-carbamic acid tert-butyl ester (5.0 g) was suspended in ethyl acetate (15 mL) under an atmosphere of nitrogen. A solution of dry hydrogen chloride in ethyl acetate (3.7 M, 60 mL) was charged to the suspension and the mixture agitated at room temperature. After stirring for a total of 2 hours the resulting suspension was filtered and washed with ethyl acetate (2×25 mL). The solid was dried in vacuo for 60 hours at 40° C. to give N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride as an off-white solid (4.14 g, 91% yield). An aliquot (6 mg) was sealed into a pin holed aluminium pan. The pan was heated using a thermal cycle of 30° C. to 256° C. at 20° C. per minute and then cooled back to 30° C. (50° C. per minute). A nitrogen flow rate of 60 mL/min was maintained over the sample during the cycle. Isolation of the white solid (6 mg) from the DSC pan afforded N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (Form 2).

An XRPD diffractogram of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (Form 2) is shown in FIG. 5.

Peak position table:

| Pos. [°2Th.] | Height [cts] | FWHM [°2Th.] | d-spacing [Å] | Rel. Int. [%] |
|---|---|---|---|---|
| 3.3070 | 1075.86 | 0.0768 | 26.71753 | 39.80 |
| 4.6799 | 950.11 | 0.1023 | 18.88250 | 35.15 |
| 5.6951 | 1856.24 | 0.0768 | 15.51845 | 68.67 |
| 5.9805 | 1039.95 | 0.1023 | 14.77853 | 38.47 |
| 6.6686 | 1014.97 | 0.0768 | 13.25511 | 37.55 |
| 7.3582 | 369.02 | 0.1279 | 12.01428 | 13.65 |
| 7.8208 | 487.46 | 0.1023 | 11.30472 | 18.03 |
| 8.2936 | 899.00 | 0.1791 | 10.66123 | 33.26 |
| 8.4475 | 806.49 | 0.0768 | 10.46733 | 29.83 |
| 8.9889 | 330.16 | 0.1023 | 9.83805 | 12.21 |
| 9.4038 | 486.45 | 0.1023 | 9.40489 | 18.00 |
| 10.0299 | 729.01 | 0.1023 | 8.81923 | 26.97 |
| 10.4931 | 624.51 | 0.1791 | 8.43091 | 23.10 |
| 10.9988 | 975.24 | 0.1023 | 8.04442 | 36.08 |
| 11.7536 | 245.09 | 0.1023 | 7.52941 | 9.07 |
| 13.1421 | 877.95 | 0.1279 | 6.73688 | 32.48 |
| 14.1298 | 189.58 | 0.2047 | 6.26812 | 7.01 |
| 15.3505 | 210.21 | 0.1535 | 5.77229 | 7.78 |
| 15.7802 | 310.59 | 0.2047 | 5.61607 | 11.49 |
| 16.7562 | 812.56 | 0.1023 | 5.29108 | 30.06 |
| 16.9866 | 1130.90 | 0.1279 | 5.21984 | 41.83 |
| 17.3077 | 810.26 | 0.1279 | 5.12370 | 29.97 |
| 18.0388 | 1199.00 | 0.3070 | 4.91767 | 44.35 |
| 18.3860 | 1333.07 | 0.0768 | 4.82559 | 49.31 |
| 18.5848 | 1711.69 | 0.1279 | 4.77440 | 63.32 |

-continued

Peak position table:

| Pos. [°2Th.] | Height [cts] | FWHM [°2Th.] | d-spacing [Å] | Rel. Int. [%] |
| --- | --- | --- | --- | --- |
| 18.9114 | 1053.68 | 0.1023 | 4.69267 | 38.98 |
| 19.7135 | 945.69 | 0.1791 | 4.50353 | 34.98 |
| 20.2996 | 767.87 | 0.2558 | 4.37480 | 28.41 |
| 21.1161 | 602.32 | 0.1535 | 4.20744 | 22.28 |
| 21.4678 | 764.85 | 0.1279 | 4.13931 | 28.29 |
| 22.1871 | 1028.96 | 0.1279 | 4.00671 | 38.06 |
| 22.7211 | 815.23 | 0.2558 | 3.91373 | 30.16 |
| 23.4683 | 678.22 | 0.2047 | 3.79080 | 25.09 |
| 24.3820 | 1401.49 | 0.1279 | 3.65077 | 51.84 |
| 25.5221 | 2703.25 | 0.2047 | 3.49021 | 100.00 |
| 26.4725 | 476.72 | 0.2047 | 3.36702 | 17.63 |
| 27.4387 | 294.02 | 0.4093 | 3.25062 | 10.88 |
| 28.1127 | 1047.80 | 0.1791 | 3.17420 | 38.76 |
| 28.9034 | 464.66 | 0.1279 | 3.08914 | 17.19 |
| 29.3333 | 255.04 | 0.1535 | 3.04484 | 9.43 |
| 30.4339 | 165.30 | 0.1535 | 2.93719 | 6.12 |
| 31.0871 | 342.59 | 0.1248 | 2.87456 | 12.67 |
| 31.8915 | 61.28 | 0.4992 | 2.81084 | 2.27 |

The DSC data for Form 2 are shown in FIG. 6.

Biological Activity

The ability of the crystalline forms of the invention to inhibit plasma kallikrein may be determined using the following biological assay:

Determination of the Ki for Plasma Kallikrein

Plasma kallikrein inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human plasma kallikrein (Protogen) was incubated at 37° C. with the fluorogenic substrate H-DPro-Phe-Arg-AFC and various concentrations of the test compound. Residual enzyme activity (initial rate of reaction) was determined by measuring the change in optical absorbance at 410 nm and the Ki value for the test compound was determined.

When tested in this assay, Form 1 showed a Ki (human Pkal) of 0.010 µM.

The crystalline forms may also be screened for inhibitory activity against the related enzyme KLK1 using the following biological assay:

Determination of the $IC_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human KLK1 (Callbiochem) was incubated at 37° C. with the fluorogenic substrate H-DVal-Leu-Arg-AFC and various concentrations of the test compound. Residual enzyme activity (initial rate of reaction) was determined by measuring the change in optical absorbance at 410 nm and the $IC_{50}$ value for the test compound was determined.

When tested in this assay, the Form 1 showed an $IC_{50}$ (human KLK1) of >10 µM.

The crystalline forms may also be screened for inhibitory activity against the related enzymes plasmin, thrombin, trypsin, Factor Xa and Factor XIIa using the following biological assays:

Determination of Enzyme Selectivity

Human serine protease enzymes plasmin, thrombin, trypsin, Factor Xa and Factor XIIa were assayed for enzymatic activity using an appropriate fluorogenic substrate. Protease activity was measured by monitoring the accumulation of liberated fluorescence from the substrate over 5 minutes. The linear rate of fluorescence increase per minute was expressed as percentage (%) activity. The Km for the cleavage of each substrate was determined by standard transformation of the Michaelis-Menten equation. The compound inhibitor assays were performed at substrate Km concentration and activities were calculated as the concentration of inhibitor giving 50% inhibition ($IC_{50}$) of the uninhibited enzyme activity (100%).

When N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride was tested in these assays, the following data were obtained:

| $IC_{50}$ (nM) | | | | |
| --- | --- | --- | --- | --- |
| Thrombin | Trypsin | Plasmin | Factor Xa | Factor XIIa |
| >40000 | 10800 | 3500 | >10000 | >10000 |

Carbonic Anhydrase I Induced Retinal Vascular Permeability Model

The activity of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride has been established using this in vivo model in the rat. Rats received an intravitreal injection (5 µL) of phosphate buffered saline (PBS), CH-3457 (a plasma kallikrein inhibitor positive control) (10 µM) or N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride ("Test Compound") (1 µM) at time 0. After 30 mins, a second intravitreal injection (5 µL) of PBS or CA-I (200 ng/eye) was given. After 15 minutes, 10% sodium fluorescein was infused and retinal vascular permeability (RVP) was measured by vitreous fluorophotometry 75 minutes following the initial IVT injections. Data for N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride ("Test Compound") are presented in FIG. 7, in which the lower dashed line indicates basal RVP following PBS/PBS and upper dashed line indicates maximal stimulation. Intravitreal injection of 1 µM N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride alone had no effect upon basal RVP compared to PBS alone (3.29±0.21 vs. 3.64±0.48). Intravitreal injection of N—[(R)-1-[(S)-1-(4-amino methyl-benzylcarbamoyl)-2-phenyl-ethylcarbamoyl]-2-(4-ethoxy-phenyl)-ethyl]-benzamide hydrochloride reduced RVP (stimulated by CA-I injection) by 53±21%.

Pharmacokinetics

A pharmacokinetic study of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride was performed to assess the ocular and systemic pharmacokinetics following a single IVT dose in pigmented (Dutch-belted) rabbits. Six rabbits per dose level were given a single, bilateral, IVT injection of 50 µL of a 4.2 µg/mL (210 ng per eye) N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride formulated in phosphate buffered saline. One rabbit was euthanized at each time point (4, 8, 24, 48, 96 and 168 hours after IVT administration) and ocular tissue concentrations of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride in the vitreous, retina/choroid and aqueous humour were measured. Serial blood samples were collected in surviving rabbits.

Ocular tissue concentration data are presented in FIG. 8, in which the solid line for each ocular tissue concentration is the average of the left and right eye of each rabbit. The decline in ocular tissue concentrations of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride ("Test Compound") was minimal over 7 days. Plasma concentrations of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride following IVT administration were below 1 ng/mL at all time points.

The invention claimed is:

1. A crystalline form of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride which exhibits at least the following characteristic X-ray powder diffraction peaks (Cu Kα radiation, expressed in degrees 2θ) at approximately 5.1, 10.3, 10.7, 18.1 and 18.6.

2. The crystalline form according to claim 1 which is characterised by an IR spectrum having peaks expressed in cm$^{-1}$ at approximately 3274, 3027, 2976, 2928, 1651, 1636, 1536, 1512, 1243 and 703.

3. The crystalline form according to claim 1, wherein the crystalline form is a hydrate containing a sub-stoichiometric amount of water with respect to the N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride in the crystalline form.

4. The crystalline form according to claim 1, wherein the crystalline form is a monohydrate.

5. A pharmaceutical composition comprising N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride in association with a pharmaceutically acceptable adjuvant, diluent or carrier, wherein the N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride is present in the composition as the crystalline form of claim 1.

6. A method of treating a patient having a disease or condition mediated by plasma kallikrein, comprising administering to a patient in need of such treatment the crystalline form of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride according to claim 1, wherein the disease or condition mediated by plasma kallikrein is selected from diabetic retinopathy, diabetic macular oedema, hereditary angioedema, pancreatitis, inflammation, hypotension, and complications from diabetes selected from cerebral haemorrhage, nepropathy, cardiomyopathy, and neuropathy.

7. The method of claim 6 wherein the disease or condition mediated by plasma kallikrein is diabetic retinopathy or diabetic macular oedema.

8. The method of claim 6 wherein the disease or condition mediated by plasma kallikrein is retinal vascular permeability associated with diabetic retinopathy and diabetic macular oedema and wherein said crystalline form is administered in a form suitable for injection into the ocular region of a patient.

9. A process for the preparation of the crystalline form of claim 1, comprising crystallising the crystalline form of claim 1 from a mixture of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride and a solvent or a mixture of solvents, wherein the mixture of solvents is acetonitrile and water or acetonitrile and dimethylsulfoxide, and said mixture is heated to a temperature of approximately 75-80° C. before being allowed to cool to room temperature.

10. The method of claim 7, wherein the method results in reducing retinal vascular permeability associated with diabetic retinopathy or diabetic macular oedema.

11. The method of claim 8, wherein the form suitable for injection into the ocular region of a patient is a form suitable for intra-vitreal injection.

12. The crystalline form according to claim 1 which exhibits at least the following characteristic X-ray powder diffraction peaks (Cu Kα radiation, expressed in degrees 2θ at approximately 5.1, 10.3, 10.7, 14.9, 17.9, 18.1 and 18.6.

13. The crystalline form according to claim 1 which exhibits at least the following characteristic X-ray powder diffraction peaks (Cu Kα radiation, expressed in degrees 2θ) at approximately 5.1, 7.8, 10.3, 10.7, 14.9, 16.6, 17.9, 18.1 and 18.6.

14. The crystalline form according to claim 1 which exhibits at least the following characteristic X-ray powder diffraction peaks (Cu Kα radiation, expressed in degrees 2θ) at approximately 5.1, 7.8, 10.3, 10.7, 13.0, 14.9, 16.6, 17.9, 18.1 and 18.6.

15. The crystalline form according to claim 1 which exhibits at least the following characteristic X-ray powder diffraction peaks (Cu Kα radiation, expressed in degrees 2θ) at approximately 5.1, 5.9, 7.8, 10.3, 10.7, 11.9, 13.0, 14.9, 15.5, 15.8, 16.6, 17.9, 18.1, 18.6, 19.6, 20.0, 20.7, 20.9, 21.6, 22.2, 22.6, 23.3, 23.7, 24.0, 24.5, 25.6, 26.7, 27.7, 28.2, 29.0, 29.6, 30.5, 31.4, 31.8, 33.0, 34.2, and 34.8.

16. The pharmaceutical composition according to claim 5, wherein the crystalline form of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride present in the composition is a hydrate containing a sub-stoichiometric amount of water with respect to the N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride in the crystalline form.

17. The pharmaceutical composition according to claim 5, wherein the crystalline form of N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride present in the composition is a monohydrate.

* * * * *